(12) United States Patent
Ante et al.

(10) Patent No.: US 9,097,151 B2
(45) Date of Patent: Aug. 4, 2015

(54) METHOD AND DEVICE FOR MEASURING THE SOOT LOAD IN THE EXHAUST GAS SYSTEMS OF DIESEL ENGINES

(75) Inventors: Johannes Ante, Regensburg (DE); Rudolf Bierl, Regensburg (DE); Stephan Heinrich, Pfeffenhausen (DE); Markus Herrmann, Regensburg (DE); Andreas Ott, Steinsberg (DE); Willibald Reitmeier, Hohenschambach (DE); Denny Schädlich, Neustadt (DE); Manfred Weigl, Sinzing / Viehhausen (DE); Andreas Wildgen, Nittendorf (DE)

(73) Assignee: Continental Automotive GmbH, Hannover (DE)

( * ) Notice: Subject to any disclaimer, the term of this patent is extended or adjusted under 35 U.S.C. 154(b) by 932 days.

(21) Appl. No.: 13/147,581

(22) PCT Filed: Feb. 1, 2010

(86) PCT No.: PCT/EP2010/051157
§ 371 (c)(1),
(2), (4) Date: Oct. 17, 2011

(87) PCT Pub. No.: WO2010/086435
PCT Pub. Date: Aug. 5, 2010

(65) Prior Publication Data
US 2012/0102924 A1 May 3, 2012

(30) Foreign Application Priority Data
Feb. 2, 2009 (DE) .................... 10 2009 007 126

(51) Int. Cl.
*F01N 3/00* (2006.01)
*F01N 9/00* (2006.01)
(Continued)

(52) U.S. Cl.
CPC ............... *F01N 9/002* (2013.01); *F01N 11/00* (2013.01); *F02D 41/1466* (2013.01);
(Continued)

(58) Field of Classification Search
CPC ... F02D 41/029; F02D 41/1495; F01N 9/002; F01N 3/0842; F01N 3/035; F01N 13/02; F01N 11/002; G01M 15/102; G01N 1/2252
USPC .................. 60/274, 285, 286, 295, 297, 311; 73/117.69, 114.71
See application file for complete search history.

(56) References Cited

U.S. PATENT DOCUMENTS

| 8,752,368 B2* | 6/2014 | Ante et al. ..................... 60/297 |
| 2006/0016174 A1* | 1/2006 | Surnilla et al. .................. 60/276 |

(Continued)

FOREIGN PATENT DOCUMENTS

| DE | 41 39 325 | 1/1993 |
| DE | 41 39 325 C1 | 1/1993 |

(Continued)

OTHER PUBLICATIONS

Machine Translation of WO 2007023035 A1, Machine Translated on Jun. 23, 2014.*

*Primary Examiner* — Thomas Denion
*Assistant Examiner* — Patrick Maines
(74) *Attorney, Agent, or Firm* — Cozen O'Connor

(57) ABSTRACT

A method and device for measuring the soot load in the exhaust gas systems of diesel engines using a sensor which is mounted downstream of a particulate filter and comprises a sensor element, to measure the operability of the particulate filter. According to the method, the soot load of the sensor element is measured resistively or capacitively using electrodes. The measuring voltage of the sensor element is controlled depending on at least one actual operating parameter of the diesel engine.

13 Claims, 2 Drawing Sheets

(51) Int. Cl.
   *F01N 11/00* (2006.01)
   *F02D 41/14* (2006.01)
   *G01N 15/06* (2006.01)
   *F02D 41/02* (2006.01)

(52) U.S. Cl.
   CPC ....... *G01N 15/0656* (2013.01); *F01N 2560/05* (2013.01); *F01N 2570/10* (2013.01); *F02D 41/0235* (2013.01); *Y02T 10/47* (2013.01)

(56) References Cited

U.S. PATENT DOCUMENTS

| | | | |
|---|---|---|---|
| 2007/0033925 A1* | 2/2007 | Berger et al. | 60/276 |
| 2007/0089478 A1* | 4/2007 | Wirth et al. | 73/1.06 |
| 2007/0204597 A1* | 9/2007 | Nakano | 60/276 |
| 2007/0251224 A1* | 11/2007 | Andrews et al. | 60/301 |
| 2007/0271903 A1* | 11/2007 | Rhodes et al. | 60/278 |
| 2007/0273540 A1* | 11/2007 | Inoue et al. | 340/632 |
| 2008/0000286 A1* | 1/2008 | Strohmaier et al. | 73/23.21 |
| 2008/0053067 A1* | 3/2008 | Schmidt et al. | 60/276 |
| 2009/0013758 A1* | 1/2009 | Baumann et al. | 73/23.33 |
| 2009/0126458 A1 | 5/2009 | Fleischer et al. | |
| 2009/0217737 A1* | 9/2009 | Dorfmueller et al. | 73/28.01 |
| 2009/0282808 A1* | 11/2009 | Andrews et al. | 60/277 |
| 2009/0295400 A1* | 12/2009 | Wilhelm | 324/452 |
| 2010/0170483 A1* | 7/2010 | Wienand et al. | 123/568.12 |
| 2012/0102924 A1* | 5/2012 | Ante et al. | 60/274 |
| 2012/0117945 A1* | 5/2012 | Krafthefer et al. | 60/274 |
| 2013/0192215 A1* | 8/2013 | Orbekk | 60/320 |
| 2014/0060015 A1* | 3/2014 | Yan et al. | 60/286 |

FOREIGN PATENT DOCUMENTS

| | | | |
|---|---|---|---|
| DE | 10 2004 007 041 A1 | 9/2005 | |
| DE | 10 2005 030 134 A1 | 1/2007 | |
| DE | 10 2005 030134 | 1/2007 | |
| DE | 10 2005 041 537 A1 | 4/2007 | |
| DE | 10 2005 053 120 A1 | 5/2007 | |
| DE | 10 2006 018 956 A1 | 10/2007 | |
| DE | 10 2006 018956 | 10/2007 | |
| DE | 10 2006 041 478 A1 | 3/2008 | |
| DE | 10 2006 041478 | 3/2008 | |
| WO | WO 2007023035 A1 * | 3/2007 | G01N 15/02 |

* cited by examiner

METHOD AND DEVICE FOR MEASURING THE SOOT LOAD IN THE EXHAUST GAS SYSTEMS OF DIESEL ENGINES

CROSS-REFERENCE TO RELATED APPLICATIONS

This is a U.S. national stage of International Application No. PCT/EP2010/051157, filed on 1 Feb. 2010. This patent application claims the priority of German Patent Application No. 10 2009 007 126.1, filed 2 February, the entire content of which application is incorporated herein by reference.

BACKGROUND OF THE INVENTION

1. Field of the Invention

The present invention relates to a method for measuring the soot load in an exhaust gas system of a diesel engine using a sensor connected downstream of a particle filter having a sensor element as a measure of the functional capability of the particle filter, in which the soot load is measured resistively or capacitively using a sensor element, wherein electrodes are formed on the sensor element and a measurement voltage is applied between the electrodes.

2. Description of the Related Art

Soot sensors, which are used in combination with particle filters in the exhaust gas systems of diesel engines, are known. The sensor elements of such soot sensors have for comb-shaped electrode structures. As the soot cover of the comb-shaped electrode structure of the sensor element increases, the electrical resistance of the electrode structure decreases, with the result that in this way the soot covering of the sensor element, and therefore the state of the particle filter which is combined therewith, can be detected. For example, the difference between an intact particle filter and a damaged particle filter can be determined using such a soot sensor.

The soot covering of the comb-shaped electrode structure or the soot precipitation thereon is therefore determined through the change in the electrical resistance or change in the capacitance of the electrode comb structure, and is used to assess the functional capability of a corresponding particle filter.

Such sensors or soot sensors are provided, in particular, for the on-board diagnostics of diesel systems with particle filters and serve to detect defects, for example in the filter ceramics of the particle filter. Since these sensors do not represent any additional benefit for the diesel system, it is only possible to use sensors which do not significantly increase the system costs. The simplest type of sensor in this context is a ceramic element loaded with soot in the exhaust gas. As mentioned, in this context this loading is measured resistively or capacitively by electrodes. However, since the particle concentration downstream of the particle filter is very low, such sensors must have a very high sensitivity. The sensitivity of the type of sensor mentioned above is, however, not sufficient for such a very low particle concentration, especially since the sensor has to be heated in order to avoid condensation of water or of other non-relevant liquids. The increased temperature even reduces the precipitation rate of soot particles on the sensor surface.

The use of such sensors with resistive or capacitive measuring equipment therefore entails problems owing to the low level of sensitivity. For this reason, other types of sensor have been used that have sufficient sensitivity based on the principle of charging and concentration-dependent transportation of charge. In addition, optical sensors have been used. However, these concepts have the disadvantage that they are very complex and therefore very expensive. In addition, these concepts also involve fundamental technical problems which have not yet been solved.

SUMMARY OF THE INVENTION

One embodiment of the present invention is based on a method for measuring the soot load in the exhaust gas system of diesel engines the permits particularly precise measurement of the soot load downstream of a particle filter with little outlay.

According to one embodiment the invention the measurement voltage of the sensor element is controlled as a function of at least one instantaneous operating parameter of the diesel engine.

To increase the sensitivity of sensors with capacitive or resistive measuring technology, the measurement can be carried out across the sensor electrodes at a high voltage. In this context, the high field strength between the electrodes ensures that even when there is a very small soot load, as is the case when the sensor is arranged downstream of the particle filter, a measurable current flows. However, since electrodes, in particular electrodes with a comb structure, with the smallest possible distances between them, are used in order to optimize the sensitivity of the sensors, flashovers can occur at the electrodes owing to the high field strength in the soot layer. Therefore, the problem indicated above cannot be solved by increasing the measurement voltage alone since in such a case the electrode structures can be destroyed.

The solution according to one embodiment of the invention is based on the realization that the maximum possible measurement voltage (without the occurrence of destruction) is not only dependent on the soot covering but also on operating parameters of the diesel engine such as the temperature of the exhaust gas, the moisture of the exhaust gas, etc. For this reason the measurement voltage is controlled here according to the invention as a function of at least one instantaneous operating parameter of the diesel engine, with the result that in this way a desired increase in the measuring sensitivity of the sensor is achieved and at the same time destruction is avoided. Such control of the measurement voltage of the sensor element as a function of at least one instantaneous operating parameter is possible and requires only little additional expenditure since the sensor for evaluating the measured value and for controlling the regeneration of the surface of the sensor element requires the engine operating data in any case. In the method according to one embodiment of the invention, the influence of at least one operating parameter on the measuring equipment is therefore taken into account. The measurement voltage is correspondingly adapted, with the result that the sensor is made more sensitive without there being a risk of destruction.

The measurement voltage of the sensor element is advantageously controlled as a function of a plurality of instantaneous operating parameters of the diesel engine.

In one particularly preferred embodiment of the method the moisture of the exhaust gas and/or the temperature of the exhaust gas is calculated from the at least one instantaneous operating parameter of the diesel engine and the optimum measurement voltage of the sensor element is acquired there from.

Within the scope of one configuration of the invention, a value for the soot load is determined from the measured current value of the sensor element and a value for the soot concentration in the exhaust gas is acquired over the time profile of the measured current value.

According to one embodiment the invention, electrodes with a comb structure are preferably used. This allows the measuring sensitivity of the sensor to be increased.

With the method according to embodiment of the invention it is possible to implement a sensor that can be used in sensitivity ranges previously only reserved for optical systems or charge transportation principles, while at the same time having a very small design and using a simple measuring principle without making stringent demands of the electronics.

The present invention also relates to a device for measuring the soot load in exhaust gas systems of diesel engines having a particle filter and a sensor connected downstream of the particle filter and whose sensor element resistively or capacitively measures the soot load using the electrodes, wherein the electrodes are formed on the sensor element and a measurement voltage is applied between the electrodes, and sensor electronics measure the current which flows across the electrodes of the sensor element and determine a value for the soot load or soot concentration in the exhaust gas from this measured current value. This device is characterized according to one embodiment of the invention in that the sensor electronics control the measurement voltage, applied between the electrodes, of the sensor element as a function of at least one instantaneous operating parameter of the diesel engine. This has the advantage that voltage flashovers due to undesired deposits on the electrodes are avoided, and therefore the sensor is effectively protected against destruction by such voltage flashovers and the associated high currents.

The sensor electronics are preferably connected to the engine control unit via a bidirectional interface in order to permit such control of the measurement voltage.

As far as the sensor element is concerned, it preferably has electrodes with a comb structure arranged at a short distance from one another. In addition, the sensor element preferably has a heating device that serves to heat the sensor element to avoid condensation of water or of other irrelevant liquids. The sensor element is preferably composed of a suitable ceramic. It is expediently attached in the exhaust gas system by a screw-in housing.

In one particularly preferred embodiment of the device according to the invention, the sensor comprises the sensor element, of a high-temperature-resistance screw-in housing and of the sensor electronics, wherein the screw-in housing is connected to the sensor electronics via a cable connection, preferably via a short cable tail. The sensor element has here on a ceramic strip the interdigital structure (comb structure) of the measuring electrodes as well as a heating structure (heating device) that brings the sensor element to a defined measuring temperature and, for the purpose of regenerating the sensor surface, can also generate temperatures up to 800° C. The measurement voltage, the measurement of the current and the temperature control, which are adapted in an inventive way, are made available or performed by the sensor electronics. As mentioned, the sensor electronics are connected to the engine control unit via a bidirectional interface. On the basis of data (operating parameters) present in the engine controller and are transmitted via the interface to the sensor electrode, the sensor electronics can, for example, calculate the temperature and moisture of the exhaust gas and make available the optimum measurement voltage. The measured current value is converted into a value for the soot load and a value for the soot concentration in the exhaust gas is calculated over the time profile of the measured current value.

Other objects and features of the present invention will become apparent from the following detailed description considered in conjunction with the accompanying drawings. It is to be understood, however, that the drawings are designed solely for purposes of illustration and not as a definition of the limits of the invention. It should be further understood that the drawings are not necessarily drawn to scale and that, unless otherwise indicated, they are merely intended to conceptually illustrate the structures and procedures described herein.

BRIEF DESCRIPTION OF THE DRAWINGS

The invention will be explained in more detail below with reference to an exemplary embodiment and in conjunction with the figures, in which.

DETAILED DESCRIPTION OF THE PREFERRED EMBODIMENTS

Figure 1:
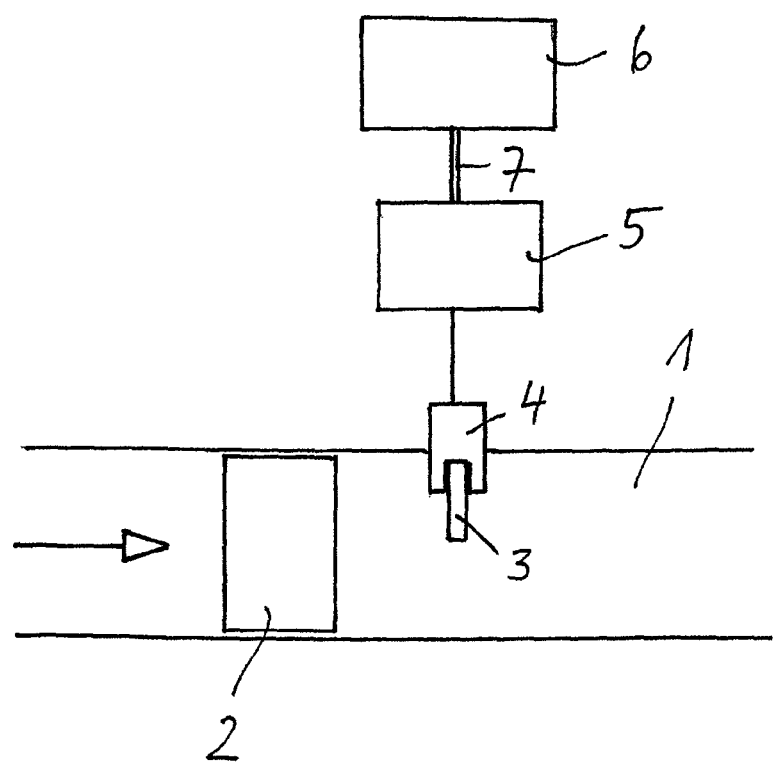
FIG. 1 is schematic design of a device for measuring the soot load in an exhaust gas system of a diesel engine.

FIG. 1 is a schematic view of an exhaust duct 1 of a diesel engine in which a particle filter 2 is arranged. The direction of flow of the exhaust gas is indicated by an arrow.

In order to monitor the functional capability of the particle filter 2, a sensor element 3 is arranged in the exhaust gas duct 1, downstream of the particle filter 2 in the direction of flow, said sensor element 3 being arranged in a high-temperature-resistant screw-in housing 4. The screw-in housing is connected via a suitable cable connection to sensor electronics 5 which are connected to the control unit 6 of the diesel engine via a bidirectional interface 7.

The sensor element 3 of the soot sensor that comprises the sensor element 3, the screw-in housing 4 and the sensor electronics 5, has an interdigital structure (comb structure) of measuring electrodes and a heater structure on a ceramic strip. The design of such a sensor element is basically known and a further explanation is not required at this point. A measurable current flows through the soot load on or at the electrode structure, wherein the measured current value is converted by the measuring electronics 5 into a value for the soot load. A value for the soot concentration in the exhaust gas is calculated over the time profile of the measured current value. The functional capability of the particle filter 2 can be inferred from this value.

The necessary measurement voltage for the sensor element 3 is made available by the sensor electronics 5, specifically as a function of operating parameters of the diesel engine. For this purpose, the sensor electronics are connected to the corresponding engine control unit 6 via a bidirectional interface 7. On the basis of data for the corresponding operating parameters, which are present in the engine controller and are transmitted to the sensor electronics via the interface, the sensor electronics 5 can, for example, calculate the moisture and the temperature of the exhaust gas and make available the optimum measurement voltage for the sensor element 3. In this way it is ensured that the sensor element 3 has a high measuring sensitivity and supplies a measurable current even when there is a small load with soot particles, without the risk of destruction of the electrode structure by flashovers.

Figure 2:
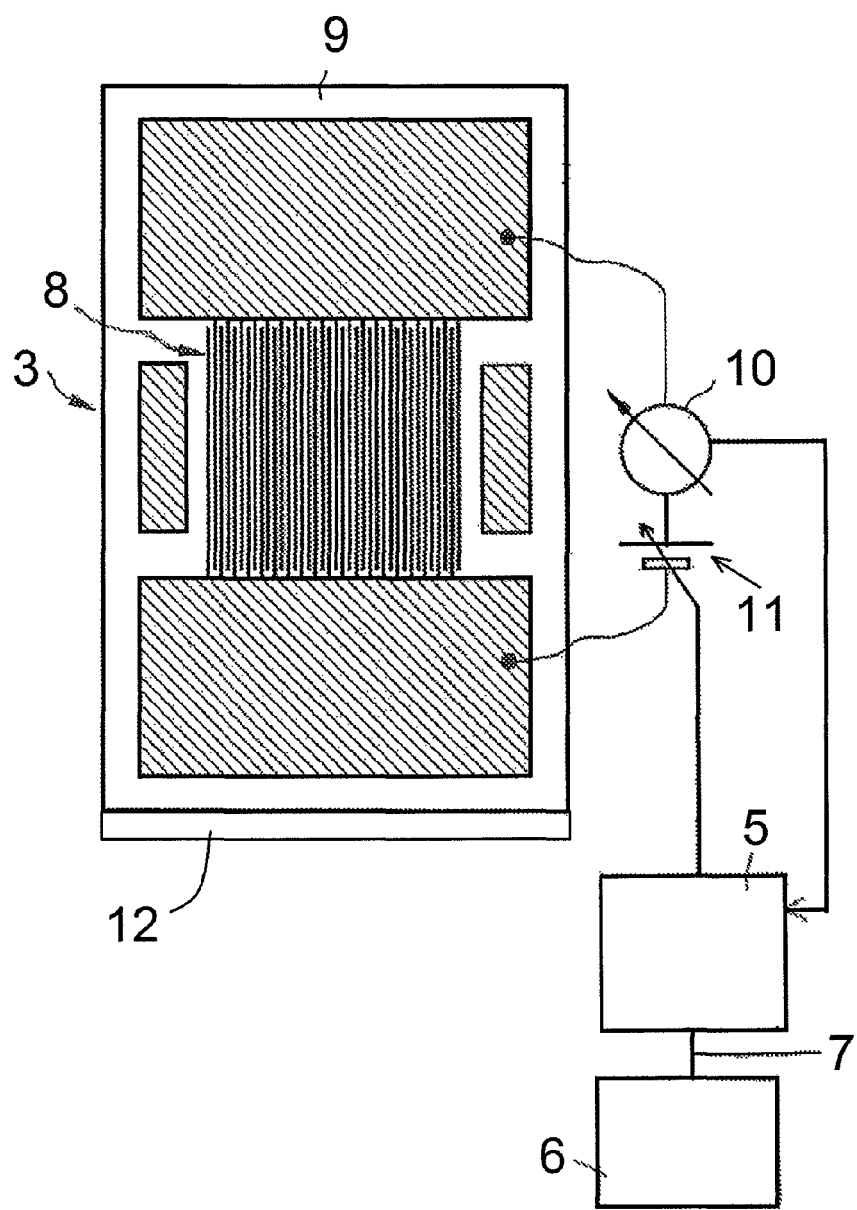
FIG. 2 is a detailed illustration of the sensor element of FIG. 1.

FIG. 2 shows a detailed illustration of the sensor element 3 which was introduced in FIG. 1. It is possible to see the sensor element, which is embodied as ceramic strips 9, and electrodes 8 arranged thereon, and heater 12, which is shown schematically. The electrodes 8 are embodied here as an interdigital comb structure. The measurement voltage of the sensor element 3 is applied between the electrodes 8. This results in an electrical field between the interdigital electrodes. If then, for example in a warming up phase of the internal combustion engine, water particles are precipitated between the electrodes 8 that engage one in the other in an interdigital fashion, the field strength between the electrodes 8 can be increased to such an extent that voltage flashovers occur between the electrodes 8, during which the current flowing across the electrodes 8 becomes so high that the electrode structure is destroyed. It is necessary to prevent this by using the controllable voltage source 11 to control the measurement voltage of the sensor element 3, applied between the electrodes, as a function of at least one instantaneous operating parameter of the diesel engine. In this example, the measurement voltage is firstly kept low. However, when the diesel engine has reached its operating temperature and the stream of exhaust gas is largely free of moisture owing to the high temperature, the measurement voltage of the sensor element 3 can be increased significantly using the controllable voltage source 11, as a result of which the soot sensor becomes significantly more sensitive to the soot particles to be measured. The measurement voltage which is applied between the electrodes 8 is therefore controlled as a function of the instantaneous operating parameters of the diesel engine. This control takes place using the sensor electronics 5 and the control unit 6 of the diesel engine.

The electrical current, which flows across the electrodes 8, is measured using the current-measuring element 10 in order to evaluate the soot load in the exhaust gas system. The current-measuring element 10 can also be used to influence the controllable voltage source 11. If, for example owing to the deposition of moisture on the electrodes 8, a voltage flashover takes place between the electrodes 8 and therefore a very high electrical current is measured by the current-measuring element 10, this information can be received by the sensor electronics 5 and processed, as a result of which the controllable voltage source 11 can be set in such a way that no further voltage flashovers occur. This ensures enduring operation of the soot sensor over a long service life since the electrodes 8 which engage one in the other in an interdigital fashion are protected against destruction. Voltages and currents in the context of this patent application are always to be understood as electrical voltages and electrical currents.

Thus, while there are shown, described and pointed out fundamental novel features of the invention as applied to preferred embodiments thereof, it will be understood that various omissions and substitutions and changes in the form and details of the illustrated apparatus, and in its operation, may be made by those skilled in the art without departing from the spirit of the invention. Moreover, it should be recognized that structures shown and/or described in connection with any disclosed form or embodiment of the invention may be incorporated in any other disclosed or described or suggested form or embodiment as a general matter of design choice.

The invention claimed is:

1. A method for measuring a soot load of an exhaust gas in an exhaust gas system of a diesel engine as a measure of functional capability of a particle filter using a sensor having a sensor element connected downstream of the particle filter, the method comprising:
   measuring the soot load one of resistively and capacitively using the sensor element, wherein electrodes are formed on the sensor element;
   applying a measurement voltage between the electrodes; and
   controlling the measurement voltage applied between the electrodes as a function of at least one instantaneous operating parameter of the diesel engine; and
   calculating at least one of a moisture of the exhaust gas and a temperature of the exhaust gas as the at least one instantaneous operating parameter of the diesel engine; and
   acquiring an optimum measurement voltage of the sensor element from the at least one of the moisture of the exhaust gas and the temperature of the exhaust gas.

2. The method as claimed in claim 1, wherein the electrodes have an inter-digital comb structure.

3. The method as claimed in claim 1, further comprising:
   measuring a current across the electrodes;
   determining a value for the soot load from the current measured across the electrodes; and
   acquiring a value for soot concentration in the exhaust gas over a time profile of the measured current value.

4. The method as claimed in claim 3, wherein the electrodes have an inter-digital comb structure.

5. A method for measuring a soot load of an exhaust gas in an exhaust gas system of a diesel engine as a measure of functional capability of a particle filter using a sensor having a sensor element connected downstream of the particle filter, the method comprising:
   measuring the soot load one of resistively and capacitively using the sensor element, wherein electrodes are formed on the sensor element;
   applying a measurement voltage between the electrodes;
   controlling the measurement voltage applied between the electrodes as a function of at least one instantaneous operating parameter of the diesel engine;
   measuring a current across the electrodes;
   determining a value for the soot load from the current measured across the electrodes; and
   acquiring a value for soot concentration in the exhaust gas over a time profile of the measured current value.

6. A device for measuring a soot load in an exhaust gas system of diesel engines having a particle filter comprising:
   a sensor element connected downstream of the particle filter, the sensor element configured to one of resistively and capacitively measure the soot load using electrodes, wherein the electrodes are formed on the sensor element and a measurement voltage is applied between the electrodes; and
   sensor electronic circuits configured to measure a current that flows across the electrodes of the sensor element and determine a value for the soot load and soot concentration in the exhaust gas from the measured current value, wherein the sensor electronic circuits are further configured to control the measurement voltage as a function of at least one instantaneous operating parameter of the diesel engine and at least one of:
      A) calculate at least one of a moisture of the exhaust gas and a temperature of the exhaust gas as the at least one instantaneous operating parameter of the diesel engine; and
      acquire an optimum measurement voltage of the sensor element from the at least one of the moisture of the exhaust gas and the temperature of the exhaust gas; and
      B) acquire a value for soot concentration in the exhaust gas over a time profile of the measured current value.

7. The device as claimed in claim 6, wherein the sensor electronic circuits are connected to an engine control unit via a bidirectional interface.

8. The device as claimed in claim 7, wherein the sensor element has electrodes with a comb structure.

9. The device as claimed in claim 8, wherein the sensor element has a heating device.

10. The device as claimed in claim 9, wherein the sensor element is attached in the exhaust gas system by a screw-in housing.

11. The device as claimed in claim 6, wherein the sensor element has electrodes with a comb structure.

12. The device as claimed in claim 6, wherein the sensor element has a heating device.

13. The device as claimed in claim 6, wherein the sensor element is attached in the exhaust gas system by a screw-in housing.

* * * * *